(12) United States Patent
Takahashi

(10) Patent No.: US 9,949,708 B2
(45) Date of Patent: Apr. 24, 2018

(54) RADIATION IMAGING APPARATUS AND METHOD OF CONTROLLING THE SAME, RADIATION IMAGE PROCESSING APPARATUS AND METHOD THEREOF, AND COMPUTER-READABLE STORAGE MEDIUM

(71) Applicant: CANON KABUSHIKI KAISHA, Tokyo (JP)

(72) Inventor: Naoto Takahashi, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 72 days.

(21) Appl. No.: 15/084,771

(22) Filed: Mar. 30, 2016

(65) Prior Publication Data
US 2016/0206270 A1 Jul. 21, 2016

Related U.S. Application Data

(63) Continuation of application No. PCT/JP2014/005144, filed on Oct. 9, 2014.

(30) Foreign Application Priority Data

Oct. 21, 2013 (JP) .................. 2013-218675
Oct. 21, 2013 (JP) .................. 2013-218676

(51) Int. Cl.
*A61B 6/00* (2006.01)
*G06T 5/00* (2006.01)
(Continued)

(52) U.S. Cl.
CPC .......... *A61B 6/5258* (2013.01); *A61B 6/4233* (2013.01); *A61B 6/4291* (2013.01); (Continued)

(58) Field of Classification Search
CPC combination set(s) only.
See application file for complete search history.

(56) References Cited

U.S. PATENT DOCUMENTS 5,671,264 A * 9/1997 Florent ..................... G06T 5/20
                                                              250/369
5,818,898 A   10/1998 Tsukamoto et al. ......... 378/98.8
(Continued)

FOREIGN PATENT DOCUMENTS

EP      2423961       2/2012
JP      2004-080749   3/2004
(Continued)

OTHER PUBLICATIONS

Extended European Search Report dated May 30, 2017 in counterpart European Patent Application 14854929.8 (in English).

*Primary Examiner* — Tsung-Yin Tsai
(74) *Attorney, Agent, or Firm* — Fitzpatrick Cella Harper and Scinto

(57) ABSTRACT

A radiation imaging apparatus acquires a radiation image from radiation detected by a radiation detection unit, corrects a first pixel that is a correction target in the radiation image by referring to a second pixel other than the first pixel, calculates an evaluation value that evaluates an increase in a noise level caused by correcting the first pixel, and performs processing of reducing the noise level for the first pixel after the correction based on the calculated evaluation value.

24 Claims, 13 Drawing Sheets

(51) Int. Cl.
*H04N 5/357* (2011.01)
*H04N 5/361* (2011.01)
*H04N 5/363* (2011.01)
*H04N 5/365* (2011.01)
*H04N 5/32* (2006.01)

(52) U.S. Cl.
CPC ............... *A61B 6/54* (2013.01); *G06T 5/002* (2013.01); *H04N 5/357* (2013.01); *H04N 5/361* (2013.01); *H04N 5/363* (2013.01); *H04N 5/365* (2013.01); *G06T 2207/10116* (2013.01); *G06T 2207/20012* (2013.01); *H04N 5/32* (2013.01)

(56) References Cited

U.S. PATENT DOCUMENTS

| | | | | |
|---|---|---|---|---|
| 6,118,850 | A * | 9/2000 | Mayo | G01N 23/2076 378/82 |
| 6,681,054 | B1 * | 1/2004 | Gindele | G06K 9/40 382/254 |
| 6,718,068 | B1 * | 4/2004 | Gindele | G06T 5/002 382/254 |
| 8,103,117 | B2 | 1/2012 | Takahashi | 382/265 |
| 8,553,783 | B2 * | 10/2013 | Deng | H04N 5/213 348/606 |
| 8,660,226 | B2 * | 2/2014 | Narayanan | H04B 1/10 375/350 |
| 2003/0097076 | A1 * | 5/2003 | Nambu | A61B 6/463 600/504 |
| 2008/0095313 | A1 * | 4/2008 | Ruhrnschopf | A61B 6/4035 378/98.4 |
| 2008/0284880 | A1 * | 11/2008 | Numata | H04N 5/217 348/241 |
| 2010/0158404 | A1 * | 6/2010 | Mathew | G06T 5/30 382/257 |
| 2010/0177980 | A1 * | 7/2010 | Bajo | G06K 9/00986 382/257 |
| 2010/0272340 | A1 * | 10/2010 | Bar-Aviv | G06T 5/20 382/131 |
| 2011/0268328 | A1 * | 11/2011 | Bar-Aviv | G06T 5/50 382/128 |
| 2012/0020541 | A1 * | 1/2012 | Hayashida | A61B 6/583 382/132 |
| 2012/0074332 | A1 | 3/2012 | Watanabe | 250/394 |
| 2012/0217410 | A1 | 8/2012 | Amitani | 250/370.09 |
| 2013/0068955 | A1 * | 3/2013 | Matsuura | G01T 1/24 250/370.09 |
| 2013/0162871 | A1 * | 6/2013 | Bosco | H04N 5/2176 348/246 |
| 2014/0126799 | A1 * | 5/2014 | Miyamoto | G06T 5/003 382/132 |
| 2014/0284491 | A1 * | 9/2014 | Sato | G01T 1/247 250/393 |

FOREIGN PATENT DOCUMENTS

| | | |
|---|---|---|
| JP | 03415348 | 3/2004 |
| JP | 2011-249891 | 12/2011 |
| JP | 2012-029720 | 2/2012 |
| JP | 2012-176155 | 9/2012 |
| JP | 2013-085632 | 5/2013 |
| WO | 2011/013390 A | 2/2011 |

* cited by examiner

CORRECTION COEFFICIENTS
WHEN GRID DOES NOT EXIST

CORRECTION COEFFICIENTS WHEN GRID EXISTS

DECREASE RATIO OF PIXEL VALUE
BEFORE PERIODIC SIGNAL REMOVAL

DECREASE RATIO OF PIXEL VALUE
AFTER PERIODIC SIGNAL REMOVAL

RADIATION IMAGING APPARATUS AND METHOD OF CONTROLLING THE SAME, RADIATION IMAGE PROCESSING APPARATUS AND METHOD THEREOF, AND COMPUTER-READABLE STORAGE MEDIUM

This application is a continuation of International Patent Application No. PCT/JP2014/005144 filed on Oct. 9, 2014, and claims priority to Japanese Patent Application Nos. 2013-218675 and 2013-218676 filed on Oct. 21, 2013, the entire contents of which are incorporated herein by reference.

TECHNICAL FIELD

The present invention relates to a technique of correcting a pixel with a radiation loss, which exits in a radiation image (for example, X-ray image).

BACKGROUND ART

In recent years, a flat panel detector (to be referred to as an FPD hereinafter) has been put into practical use, which accumulates X-rays as a charge signal, converts it into a digital signal, and provides a diagnostic image. Such an X-ray imaging apparatus is configured to execute imaging by synchronizing X-ray irradiation of an X-ray generation apparatus and an imaging operation of the FPD.

There are also many market requirements for replacing the film or imaging plate portion of an existing modality with an FPD. When replacing the imaging unit of an existing modality with an FPD, it may be difficult to build an interface to synchronize the X-ray generation apparatus with the FPD. PTL 1 proposes an FPD that detects X-ray irradiation on the FPD side and automatically starts the accumulation operation without providing the interface between the X-ray generation apparatus and the FPD.

However, in the case in which X-ray irradiation is automatically detected on the FPD side to start the accumulation operation, X-ray irradiation needs to be performed to some extent until the FPD detects X-rays and starts the accumulation operation, and a reset operation is performed during this time. For this reason, charges accumulated by X-rays to irradiate from the start of actual X-ray irradiation to the start of the accumulation operation upon detecting the X-rays are removed. The removed charges cannot contribute to output values. Hence, even if the incident X-ray amount is the same, the output value changes between a pixel whose X-ray information is lost upon charge removal (this pixel will be referred to as an X-ray deficiency pixel hereinafter) and a pixel from which charges are not removed (this pixel will be referred to as an X-ray non-deficiency pixel hereinafter).

For example, in PTL 1, the reset operation at the time of X-ray detection is performed for every other line. Since the reset operation is performed alternately for even-numbered lines and odd-numbered lines on a frame basis, charge removal is performed for every other line from X-ray irradiation to the start of the accumulation operation. As a result, a line from which charges are removed (this line will be referred to as an X-ray deficiency line hereinafter) and a line without charge removal (this line will be referred to as an X-ray non-deficiency line hereinafter) alternately occur, and the output value difference between the lines appears as a stripe pattern on the image. Note that concerning this problem, PTL 1 discloses a method of discarding the data of X-ray deficiency lines as defects and correcting them by linear interpolation of peripheral pixels.

As a method other than that described above, there has recently been proposed a method of obtaining the X-ray deficiency ratio of an X-ray deficiency line based on an X-ray non-deficiency line adjacent to the X-ray deficiency line and digitally amplifying the output value in accordance with the deficiency ratio. This method can effectively use the output value of an X-ray deficiency line and therefore obtain a more appropriate correction result, as compared to the method of discarding the information of an X-ray deficiency line as a defect.

CITATION LIST

Patent Literature

PTL 1: Japanese Patent Laid-Open No. 2011-249891

SUMMARY OF THE INVENTION

Technical Problem

In an X-ray image including X-ray deficiency pixels (X-ray deficiency lines) and X-ray non-deficiency pixels (X-ray non-deficiency lines), it is important to appropriately correct the X-ray deficiency pixels (X-ray deficiency lines), regardless of whether they are generated by the above-described automatic X-ray detection and the reset operation of the FPD. This is because the X-ray deficiency pixels in an X-ray image or inappropriately corrected X-ray deficiency pixels have an influence on diagnostic interpretation by a doctor.

However, if an output value is amplified in accordance with the deficiency ratio of an X-ray deficiency line in an X-ray image, as described above, not only the signal but also superimposed noise is amplified together. Hence, if driving described in PTL 1 is used, the noise level changes between an X-ray deficiency line and an X-ray non-deficiency line which are adjacent to each other, although the incident X-ray amounts are almost the same, resulting in an unnatural image.

An aspect of the present invention provides a correction method capable of suppressing deterioration of a noise level that occurs when correcting a pixel.

Solution to Problem

A radiation imaging apparatus according to one aspect of the present invention has the following arrangement. That is, the radiation imaging apparatus comprises: an acquisition unit configured to acquire an X-ray image from X-rays detected by radiation detection unit; a correction unit configured to correct a first pixel that is a correction target in the radiation image by referring to a second pixel other than the first pixel; a calculation unit configured to calculate an evaluation value that evaluates an increase in a noise level caused when the first pixel is corrected by the correction unit; and a reduction unit configured to perform processing of reducing the noise level for the first pixel after the correction based on the evaluation value calculated by the calculation unit.

Advantageous Effects of Invention

According to the present invention, it is possible to suppress deterioration of a noise level that occurs when correcting a pixel.

Other features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

First Embodiment

Figure 1:
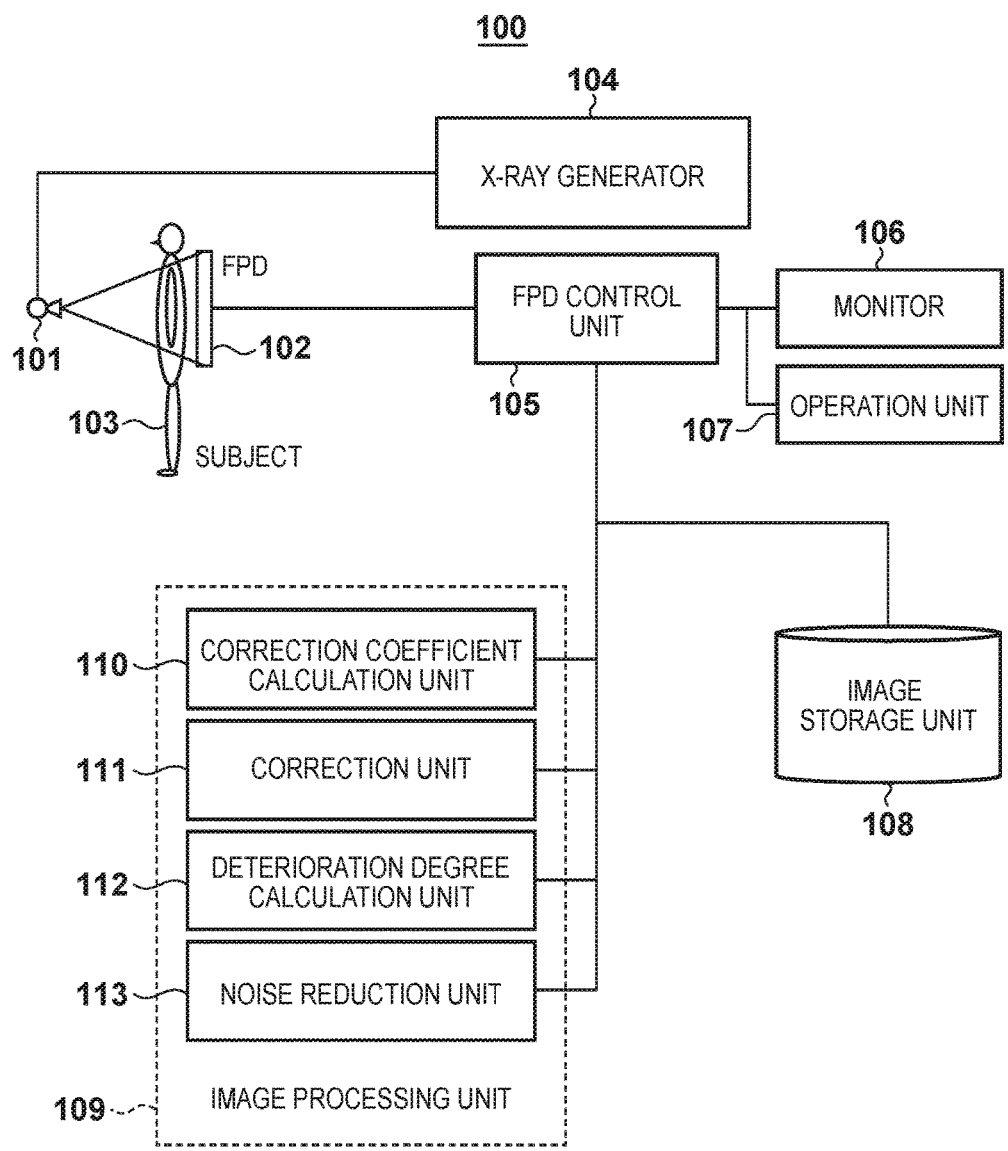
FIG. 1 is a block diagram showing an example of the arrangement of an X-ray imaging apparatus according to the first embodiment.

A preferred embodiment of the present invention will now be described with reference to the accompanying drawings. The present invention is applied to a radiation imaging apparatus that acquires a radiation image from a radiation amount detected by a radiation detection unit configured to detect radiation and performs radiation image processing, for example, an X-ray imaging apparatus 100 as shown in FIG. 1. The X-ray imaging apparatus 100 has a function of executing X-ray image processing for correcting an X-ray deficiency pixel generated in an X-ray image by an X-ray loss caused by a reset operation when the X-ray image is acquired by automatically detecting X-ray irradiation.

In the above-described X-ray imaging apparatus 100, an X-ray tube 101 irradiates a subject 103 with X-rays. When an exposure switch (not shown) is pressed, an X-ray generator 104 gives a high-voltage pulse to the X-ray tube 101 to generate X-rays. Under the control of an FPD control unit 105, an FPD 102 converts the X-rays transmitted through the subject 103 into visible light by a phosphor and detects the light by a photodiode. The detected electrical signal is A/D-converted and transmitted to the FPD control unit 105. The FPD control unit 105 includes an image processing unit 109 and an image storage unit 108, and incorporates one or a plurality of computers (not shown).

The computer provided in the FPD control unit 105 includes, for example, a main control unit such as a CPU, and a storage unit including a ROM (Read Only Memory) and a RAM (Random Access Memory). The computer may also include a graphic control unit such as a GPU (Graphics Processing Unit), a communication unit such as a network card, and an input/output unit such as a keyboard, a display, or a touch panel. These components are connected by a bus or the like and controlled when the main control unit executes programs stored in the storage unit. A monitor 106 displays a received digital signal or a digital signal processed by the image processing unit 109 as an image. An operation unit 107 inputs an instruction from a user to the image processing unit 109 or the FPD 102. The image storage unit 108 stores a digital signal output from the FPD control unit 105 or image data processed by the image processing unit 109. The image processing unit 109 corrects an X-ray deficiency pixel in an image captured by the FPD 102, and includes a correction coefficient calculation unit 110, a correction unit 111, a deterioration degree calculation unit 112, and a noise reduction unit 113.

Figure 2:
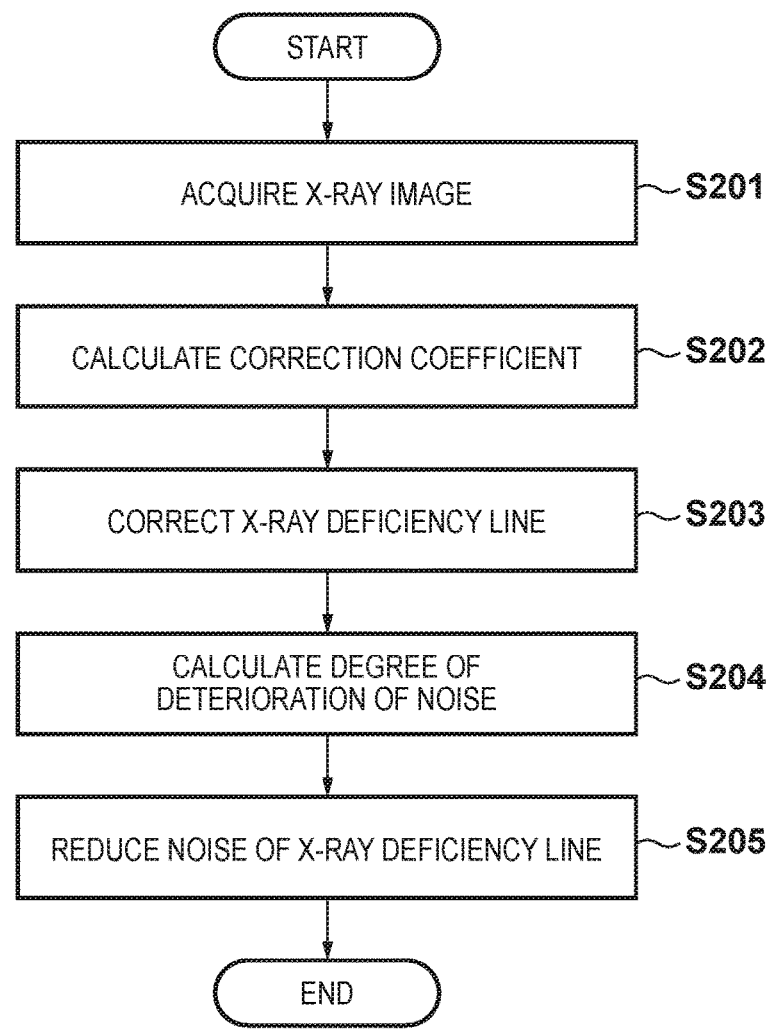
FIG. 2 is a flowchart showing a processing procedure according to the first embodiment.

The operation of the X-ray imaging apparatus 100 according to this embodiment with the above-described arrangement will be described in detail with reference to the flowchart shown in FIG. 2. First, the X-ray generator 104 applies a high-voltage pulse to the X-ray tube 101 to irradiate the subject 103 with X-rays. After the start of X-ray irradiation, the FPD 102 automatically detects the X-ray irradiation and thus starts an accumulation operation, thereby acquiring an X-ray image (step S201).

Figure 3:
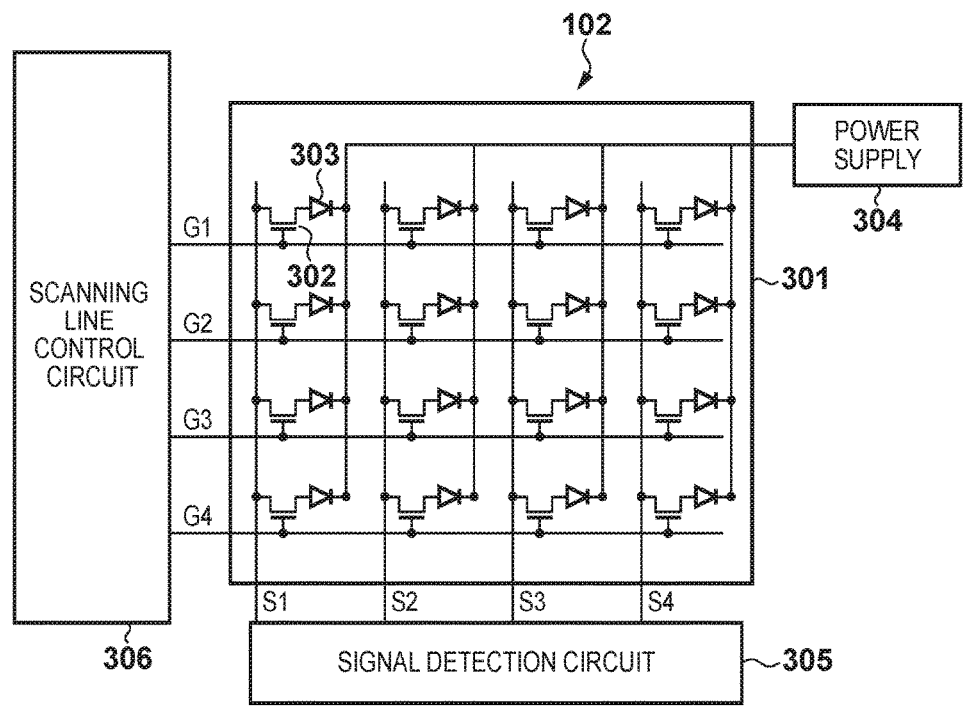
FIG. 3 is a block diagram for explaining the circuit arrangement of an FPD.

Driving for automatically detecting and determining the start of X-ray irradiation will be described here in detail with reference to FIGS. 3 to 5. FIG. 3 shows the circuit arrangement of the FPD 102. The FPD 102 includes pixels each formed from a TFT 302 and a photodiode 303. Several thousand pixels are formed in the vertical and horizontal directions on a glass substrate 301. Note that FIG. 3 illustrates a FPD including 4×4 pixels for the descriptive convenience. A scanning line control circuit 306 sequentially applies an ON signal to G1 to G4 to turn on the switches of the TFTs 302. G1 to G4 are scanning lines. When the ON signal is applied to each scanning line, the TFTs 302 are turned on, and the output charges of the photodiodes 303 are read out on a line basis. S1 to S4 are signal lines. The charges read out from the photodiodes 303 are transmitted through the signal lines and read by a signal detection circuit 305. The signal detection circuit 305 performs processes such as holding, amplification, and A/D conversion for each read signal and outputs it to the FPD control unit 105 as a digital signal. A power supply 304 supplies an operating voltage to the photodiodes 303.

Figure 4:
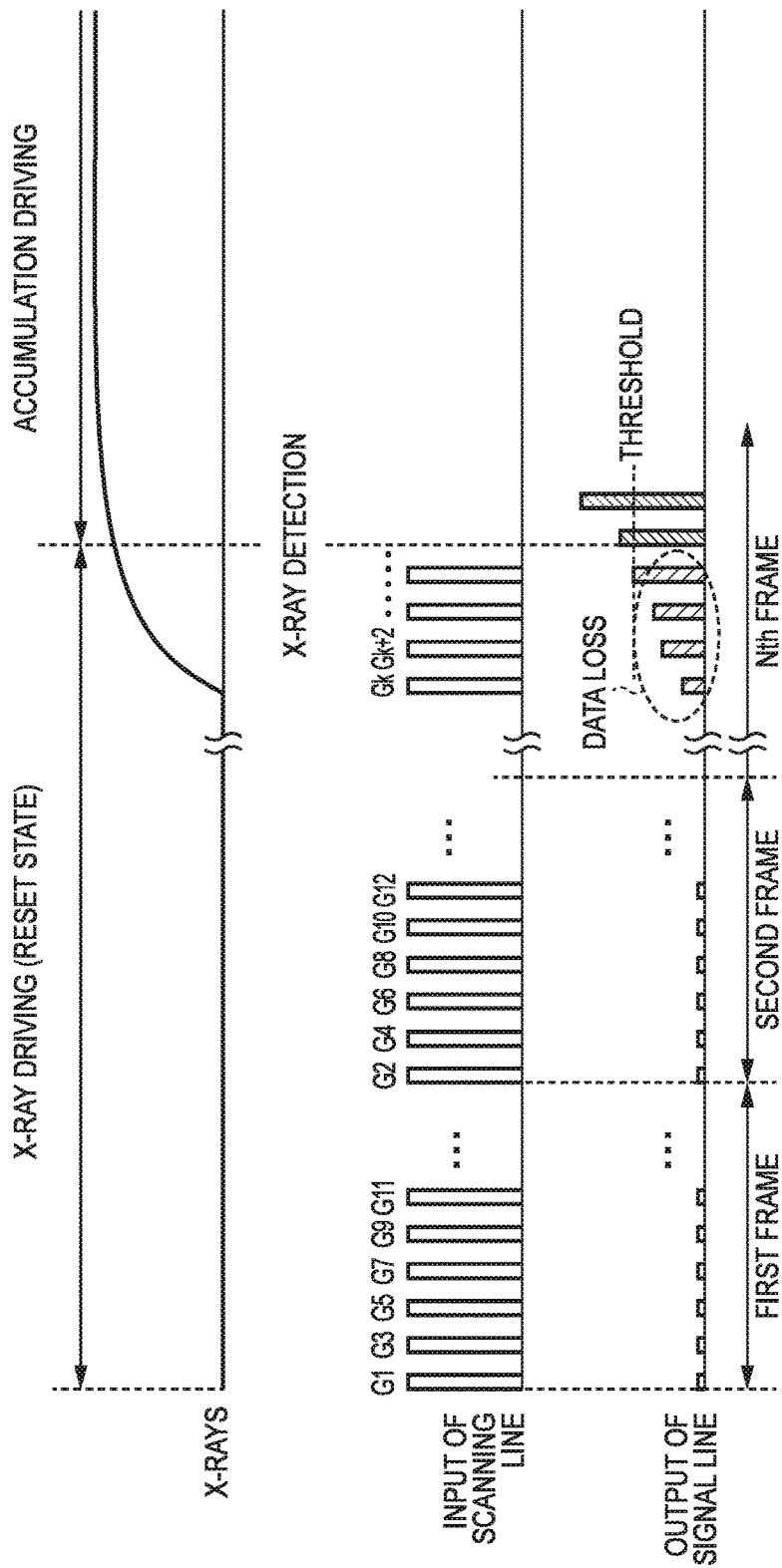
FIG. 4 is a timing chart for explaining driving of the FPD.

FIG. 4 is a timing chart showing driving of the FPD 102 according to this embodiment. When X-ray irradiation is not being performed, the FPD 102 stands by in X-ray detection driving. At this time, in the first frame, the scanning line control circuit 306 sequentially drives only the odd-numbered scanning lines G1, G3, . . . . The scanning line control circuit 306 then reads the dark charges of the pixels connected to the odd-numbered scanning lines and resets the pixels. In the second frame, the scanning line control circuit 306 sequentially drives only the even-numbered scanning lines G2, G4, . . . , and resets the pixels connected to the even-numbered scanning lines. In this way, odd-numbered lines are reset in odd-numbered frames, and even-numbered lines are reset in even-numbered frames, thereby alternately resetting the odd-numbered lines and the even-numbered lines.

The signal detection circuit 305 of the FPD control unit 105 monitors the reset charges to detect X-ray irradiation. When irradiated with X-rays, the photodiode 303 generates charges, and therefore, the output of the signal line rises. When the output exceeds a predetermined threshold, the FPD control unit 105 determines that X-ray irradiation is performed, and turns off all TFTs 302, thereby starting the accumulation operation.

The smaller the above-described threshold to detect X-ray irradiation is, the more quickly the X-ray irradiation can be detected. However, a detection error by noise or the like readily occurs. Hence, considering such an operation error, the threshold needs to be set large to some extent. As a result, not a little time lag occurs from the start of X-ray irradiation up to detection of the X-ray irradiation. Because of this time lag, charges generated by the X-rays to irradiate until the start of the accumulation operation cannot contribute to the output value, and the value becomes smaller than a proper output value. That is, a correction target line in which correction target pixels (to be referred to as deficiency pixels in this specification) each having an X-rays loss are arranged is generated.

Figure 5:
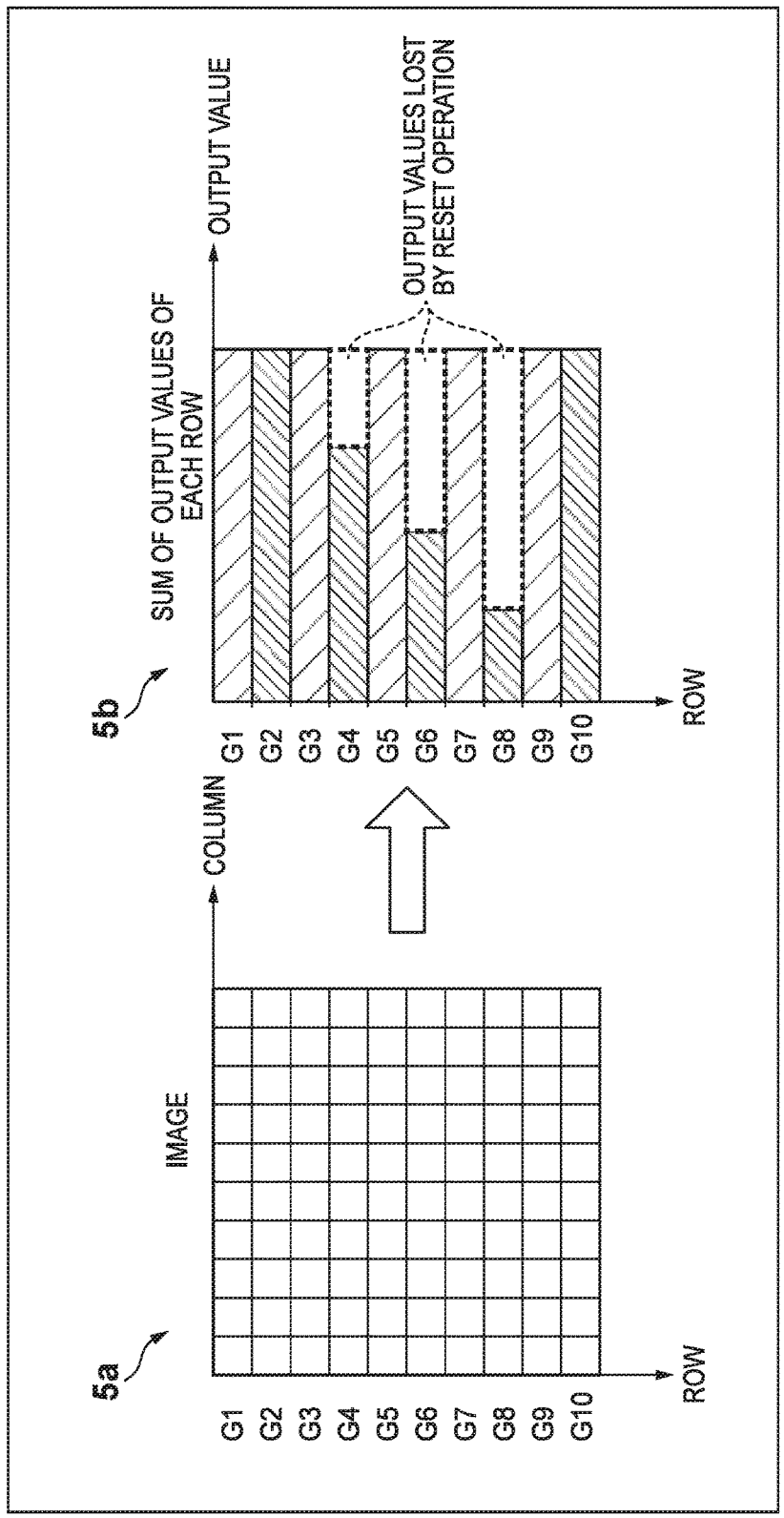
FIG. 5 is a view for explaining a decrease in the output value of an X-ray deficiency line.

FIG. 5 is a schematic view showing a decrease in an output value in a case in which the FPD is irradiated with uniform X-rays. In an image 5*a* shown in FIG. 5, one pixel is represented by one rectangle. In 5*b* of FIG. 5, the sum of output values in each row of the image 5*a* is represented by a bar graph. Note that in the case in which the FPD is irradiated with uniform X-rays, if no time lag exists until detection of X-ray irradiation, the sums of output values in the rows almost equal. Assume that X-ray irradiation starts in the even-numbered line G4, and the X-ray irradiation is detected in the even-numbered line G8. In this case, in the even-numbered lines G4, G6, and G8 where the reset operation is performed, the X-rays are lost, and the output values are smaller than the proper values, as shown in the graph 5*b*. The lines G4, G6, and G8 are correction target lines. On the other hand, the X-ray loss by the reset operation does not take place in the remaining lines. These lines are non-correction target lines that need not be corrected (that is, pixels other than the correction target pixels, which will be referred to as non-correction target pixels hereinafter).

Note that the decrease in the output value depends on the time lag from the start of X-ray irradiation to the reset operation. The larger the time lag is, the larger the decrease is. Hence, in the operation according to this embodiment, since the reset operation is sequentially performed from G1, the decrease in the output value becomes large from G4 where X-ray irradiation starts to G6, G8, . . . , as shown in the graph 5*b*.

An X-ray image obtained by the above-described operation has a portion where correction target lines in which correction target pixels are arranged and non-correction target lines in which non-correction target pixels are arranged alternately exist. This X-ray image is transferred to the image processing unit 109, and the correction target lines (to be referred to as X-ray deficiency lines hereinafter) each having a decreased output value are corrected. A detailed correction method will be described below.

First, the correction coefficient calculation unit 110 calculates a correction coefficient used to correct the output value of an X-ray deficiency line (step S202). Normally, an output value V of each pixel (the output value of each pixel will sometimes be referred to as a pixel value hereinafter) is decided by the sum of a gain component proportional to an X-ray amount X incident on the pixel and an offset component D generated by a dark current or the like. Letting A be a proportionality constant, the relationship between the output value V and the X-ray amount X is given by $$V = A \cdot X + D \tag{1}$$

On the other hand, in a pixel value $V_d$ of an X-ray deficiency line, the X-ray amount X incident on the pixel is partially lost by the reset operation, and the X-ray amount contributing the pixel value decreases to 1/G. Hence, the relationship between the pixel value $V_d$ of the X-ray deficiency line and the X-ray amount X is given by $$V_d = A \cdot X/G + D \tag{2}$$

Hence, the relationship between the pixel value $V_d$ of the X-ray deficiency line and the proper pixel value V is given by $$V = G \cdot (V_d - D) + D \tag{3}$$

Note that the values G and D in equation (3) are unknown. When the two values are calculated as correction coefficients, the pixel value $V_d$ of the X-ray deficiency line can be corrected to the proper pixel value V.

Figure 6:
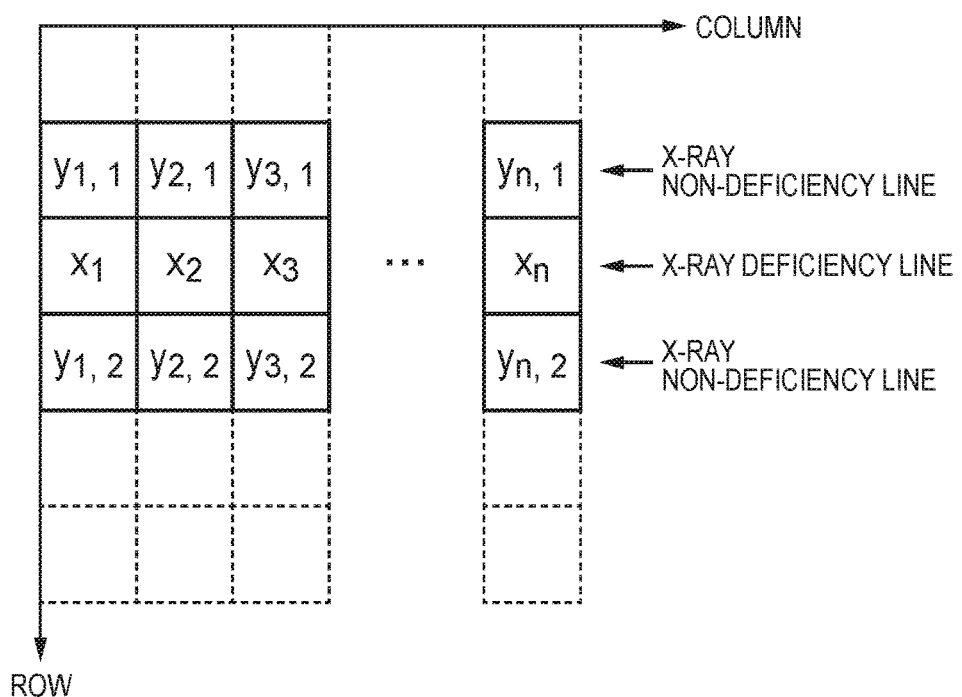
FIG. 6 is a view for explaining a correction coefficient calculation method.

In this embodiment, the correction coefficients G and D are calculated by regression analysis using the pixels of an X-ray non-deficiency line (that is, a non-correction target line) that is adjacent and highly correlated with the X-ray deficiency line. More specifically, as shown in FIG. 6, let $\{x_i | i=1, 2, \ldots, n\}$ be the pixel values in columns i of the X-ray deficiency line, and $\{y_{i,1} | i=1, 2, \ldots, n\}$ and $\{y_{i,2} | i=1, 2, \ldots, n\}$ be the pixel values in the columns i of the X-ray non-deficiency lines adjacent in the vertical direction. When the pixel values of each column are assumed to be almost the same, the relationship between a pixel value x of the X-ray deficiency line and a pixel value y of the X-ray non-deficiency line is given by $$\begin{aligned} y_{i,j} &= G \cdot (x_i - D) + D \\ &= G \cdot x_i + D \cdot (1 - G) \end{aligned} \tag{4}$$

As indicated by equation (4), the relationship between x and y is represented by a linear expression of the gradient G and the intercept D·(1−G). G and D can be calculated by linear regression analysis. For example, least square regression is used as the method of linear regression analysis, a gradient $\underline{a}$ and an intercept b, which minimize an error E given by equation (5), are obtained, and the correction coefficients G and D are calculated by equation (6) based on the obtained gradient $\underline{a}$ and the intercept b.

$$E = \sum_{j=1}^{2} \sum_{i=1}^{n} (y_{i,j} - a \cdot x_i - b)^2 \tag{5}$$

$$G = a, D = \frac{b}{1-a} \tag{6}$$

In this embodiment, the method using least square regression has been described. However, the present invention is not limited to this method, and the correction coefficients can similarly be calculated even using an already known method such as MA regression or RMA regression. In this embodiment, the correction coefficients are obtained assuming that the pixel values of each column are almost the same. However, if a steep edge or the like exists, pixels for which the assumption cannot hold exist. Hence, as a measure against such outliers, known robust regression such as M estimation, LMedS estimation, or RANSAC may be used.

The method of calculating the correction coefficients G and D for one X-ray deficiency line has been described above. The same processing as described above is performed for all X-ray deficiency lines, and the correction coefficients G and D for each X-ray deficiency line are calculated. Note that since the timing at which X-ray irradiation starts is unknown, the line as the end of X-ray deficiency lines is unknown. Hence, in this embodiment, whether a line is a correction target line is determined in the following way. That is, the lines that have undergone the reset operation are sequentially traced back from the line that has undergone the reset operation at the timing of X-ray irradiation detection, thereby selecting correction target lines (X-ray deficiency lines). The correction coefficients of the selected correction target lines (X-ray deficiency lines) are obtained. The correction coefficients G and D are calculated up to the line whose correction coefficient G falls within a predetermined range, for example, about 1. For example, in the graph 5b, the correction coefficients G and D are obtained sequentially from G8 that has undergone the reset operation at the timing of X-ray irradiation detection to G6 and G4. The correction coefficient calculation ends when the correction amount falls within a predetermined range. For example, the correction coefficient calculation ends at the line G2 whose correction coefficient G is about 1. Note that the correction target lines may be obtained by tracing back a predetermined number of lines from the line that has undergone the reset operation at the timing of X-ray irradiation detection. In this case, as the predetermined number, a sufficient line count is obtained in advance by calculation or an experiment.

Next, the correction unit 111 corrects the deficiency pixels of the deficiency lines using the obtained correction coefficients G and D (step S203). More specifically, let $\{V_d(i)|i=1, 2, \ldots, n\}$ be the pixel values in the columns i of the X-ray deficiency line and G and D be the correction coefficients for the line. A pixel value V(i) after correction is calculated for all X-ray deficiency lines by $$V(i)=G \cdot (V_d(i)-D)+D \tag{7}$$

Next, the deterioration degree calculation unit 112 calculates the degree of deterioration of noise for each of all the corrected pixels (step S204). Here, an evaluation value is calculated based on a noise level increased by the above-described correction from a noise level in an X-ray amount corresponding to the pixel value of a correction target pixel before correction and a noise level in an X-ray amount corresponding to the pixel value after correction. Hence, the evaluation value represents the degree of deterioration of the noise level caused by the correction. In the noise level superimposed on the output of each pixel, normally, quantum noise proportional to the X-ray amount incident on the pixel and system noise that is unique to the system and independent of the X-ray amount are dominant. Letting $\sigma_Q$ be the standard deviation of quantum noise and $\sigma_S$ be the standard deviation of system noise, a standard deviation $\sigma$ of noise superimposed on the output of each pixel is given, based on additivity of dispersion, by $$\sigma = \sqrt{\sigma_Q^2 \cdot X + \sigma_S^2} \tag{8}$$

On the other hand, in a pixel of an X-ray deficiency line, the X-ray amount X incident on the pixel is partially lost by the reset operation, and the X-ray amount contributing the output decreases to 1/G. Hence, the standard deviation $\sigma_d$ of noise superimposed on the output of the pixel of the X-ray deficiency line is given by $$\sigma_d = \sqrt{\sigma_Q^2 \cdot x/G + \sigma_S^2} \tag{9}$$

In the X-ray deficiency line corrected by equation (7), the signal component included in the output value of the pixel is multiplied by G that is the magnification of correction, and the noise is also multiplied by G. Hence, a standard deviation $\sigma_C$ of noise superimposed on the output value of the pixel of the X-ray deficiency line after correction is given by $$\sigma_C = G \cdot \sigma_d = \sqrt{G \cdot \sigma_Q^2 \cdot X + G^2 \cdot \sigma_S^2} \tag{10}$$

Hence, the noise level included in the output value of the pixel of the corrected X-ray deficiency line increases to $\sigma_C/\sigma$ times relative to the noise level included in the proper output value of the pixel (the output value when the X-ray amount is X). Hence, for each pixel, this value is calculated as an evaluation value (to be referred to as a noise deterioration degree W hereinafter) representing an increase in the noise level. A detailed calculation method is represented by $$W = \sqrt{\frac{G \cdot \sigma_Q^2 \cdot X + G^2 \cdot \sigma_S^2}{\sigma_Q^2 \cdot X + \sigma_S^2}} \tag{11}$$

Here, the standard deviation $\sigma_Q$ of quantum noise and the standard deviation $\sigma_S$ of system noise are values uniquely decided by the imaging system. Values calculated in advance are held in advance and used. The incident X-ray amount X can be calculated using the relationship of equation (1) described above. More specifically, letting V(i, j) be the pixel value of the corrected image V on the ith row and the jth column, an X-ray amount X(i, j) incident on each pixel can be calculated by $$X(i,j) = \frac{\overline{V}(i,j) - D}{A}, \overline{V}(i,j) = \frac{1}{(2 \cdot N + 1)^2} \sum_{\Delta i = N}^{N} \sum_{\Delta j = -N}^{N} V(i + \Delta i, j + \Delta j) \tag{12}$$

where N decides a filter size to remove the influence of noise. In this embodiment, N is set to, for example, 2. Additionally, A is a proportionality constant used to convert the X-ray amount X into the pixel value V, which is a value uniquely decided by the sensor. Hence, a value calculated in advance is held in advance and used.

Next, the noise reduction unit 113 performs noise reduction of all the corrected pixels (step S205). Assuming that adjacent pixels have the same noise level, the noise level of a corrected X-ray deficiency pixel is corrected so as to be almost equivalent to that of adjacent X-ray non-deficiency pixels.

In this embodiment, the noise of a corrected X-ray deficiency pixel is reduced by weighted addition (filtering) of three points, that is, the corrected X-ray deficiency pixel and the adjacent X-ray non-deficiency pixels on the upper and lower sides. More specifically, letting V(i, j) be the pixel value of the corrected image V on the ith row and the jth column, the noise of the X-ray deficiency pixel is reduced by $$V_N(i, j) = a \cdot V(i, j) + \frac{1-a}{2} \cdot (V(i-1, j) + V(i+1, j)) \quad (13)$$

where $\underline{a}$ is the weight coefficient that decides the degree of noise reduction, which is set such that the noise level of the corrected pixel V(i, j) becomes almost equivalent to that of adjacent pixels V(i−1, j) and V(i+1, j). A method of deciding $\underline{a}$ will be described below.

Letting $\sigma_T$ be the standard deviation of noise superimposed on the output of the corrected X-ray deficiency pixel and $\sigma_R$ be the standard deviation of noise superimposed on the output of an adjacent pixel, the standard deviation $\sigma$ of noise superimposed on the output after noise reduction is given by $$\sigma^2 = a^2 \cdot \sigma_T^2 + \frac{(1-a)^2}{2} \cdot \sigma_R^2 \quad (14)$$

The condition that makes the noise level of the corrected pixel V(i, j) almost equivalent to that of the adjacent pixels V(i−1, j) and V(i+1, j) is $$\sigma = \sigma_R \quad (15)$$

In addition, the relationship between $\sigma_T$ and $\sigma_R$ is given, based on the noise deterioration degree W, by $$\sigma_R = W \cdot \sigma_T \quad (16)$$

When equations (15) and (16) are substituted into equation (14) and rewritten, we obtain $$(W^2+1) \cdot a^2 - 2 \cdot a - 1 = 0 \quad (17)$$

Hence, $\underline{a}$ is set to meet the condition of equation (17), that is, by $$a = \frac{1 + \sqrt{W^2 + 2}}{W^2 + 1} \quad (18)$$

The weight coefficient $\underline{a}$ is a value depending on the deterioration degree W. Hence, $\underline{a}$ for each pixel is calculated based on the deterioration degree calculated for the pixel by the deterioration degree calculation unit 112, and noise correction is performed.

Note that in the above embodiment, noise of an X-ray deficiency pixel is reduced using two pixels on the upper and lower sides. However, the present invention is not limited to this, and noise reduction may be performed using, for example, six pixels including pixels in the diagonal directions as well. In this embodiment, the method of reducing noise by a linear filter is used. However, the present invention is not limited to this, and, for example, a nonlinear filter such as an ε filter or bilateral filter that saves an edge may be used.

In the above embodiment, a case in which correction target lines in which correction target pixels are arranged and non-correction target lines in which non-correction target pixels are arranged alternately exist has been described. However, the present invention is not limited to this. For example, the correction and noise level reduction according to the embodiment can be applied to any image in which correction target pixels with an X-ray loss are arranged so as to be correctable by non-correction target pixels without an X-ray loss. Hence, for example, the processing may be applied to not an arrangement that performs reset on a line basis but an arrangement that performs reset on a column basis. The above-described processing is also applicable to an X-ray image in which, for example, correction target pixels and non-correction target pixels are arrayed in a checkered pattern, as a matter of course. In the above embodiment, an example in which reset is performed for each line as the reset operation on a line basis has been described. However, a plurality of even-numbered lines or odd-numbered lines (for example, "G2 and G4" and "G6 and G8" in FIG. 5) may simultaneously be reset.

Second Embodiment

Not only an X-ray loss caused by a reset operation as described above but also a signal irrelevant to the subject may be superimposed on an X-ray image. For example, in some cases, imaging is performed using an instrument called a grid that is arranged between a subject and a radiation receiving surface and configured to remove scattered rays generated when X-rays pass through the interior of the subject. This grid is formed by alternately arranging a radiation shielding substance such as lead and a radiation transmission substance such as aluminum or carbon at a predetermined width, thereby removing scattered rays. However, when the grid is arranged, some of direct rays passing through the radiation shielding substance are also removed, and therefore, periodic signals (also called grid stripes) are generated on the image.

Not only the reset operation but also the above-described X-ray deficiency lines and X-ray deficiency pixels degrade image quality. To correct them is necessary to obtain an appropriate diagnostic image. However, in some case, if X-ray information changes due to another factor such as a grid, such a change in the X-ray information adversely affects correction of the above-described X-ray deficiency pixels, and the image is further degraded by the correction. For example, when the grid is arranged under the condition that the direction of the strips of the grid becomes parallel to the direction of scanning lines, the direction of stripes caused by X-ray deficiency lines generated when X-rays are automatically detected matches the direction of the stripes of the grid. In this case, the method described in PTL 1 cannot perform appropriate correction because the stripes interfere with each other, and the correction may lead to poorer image quality. Note that the above-described problem can be solved by arranging the grid such that the direction of the stripes of the grid becomes perpendicular to the direction of the scanning lines. However, the grid may be arranged wrongly, and in this case, appropriate correction may be impossible.

The second embodiment provides an apparatus and method capable of determining whether a correction target pixel with a radiation loss is appropriately corrected.

Figure 7:
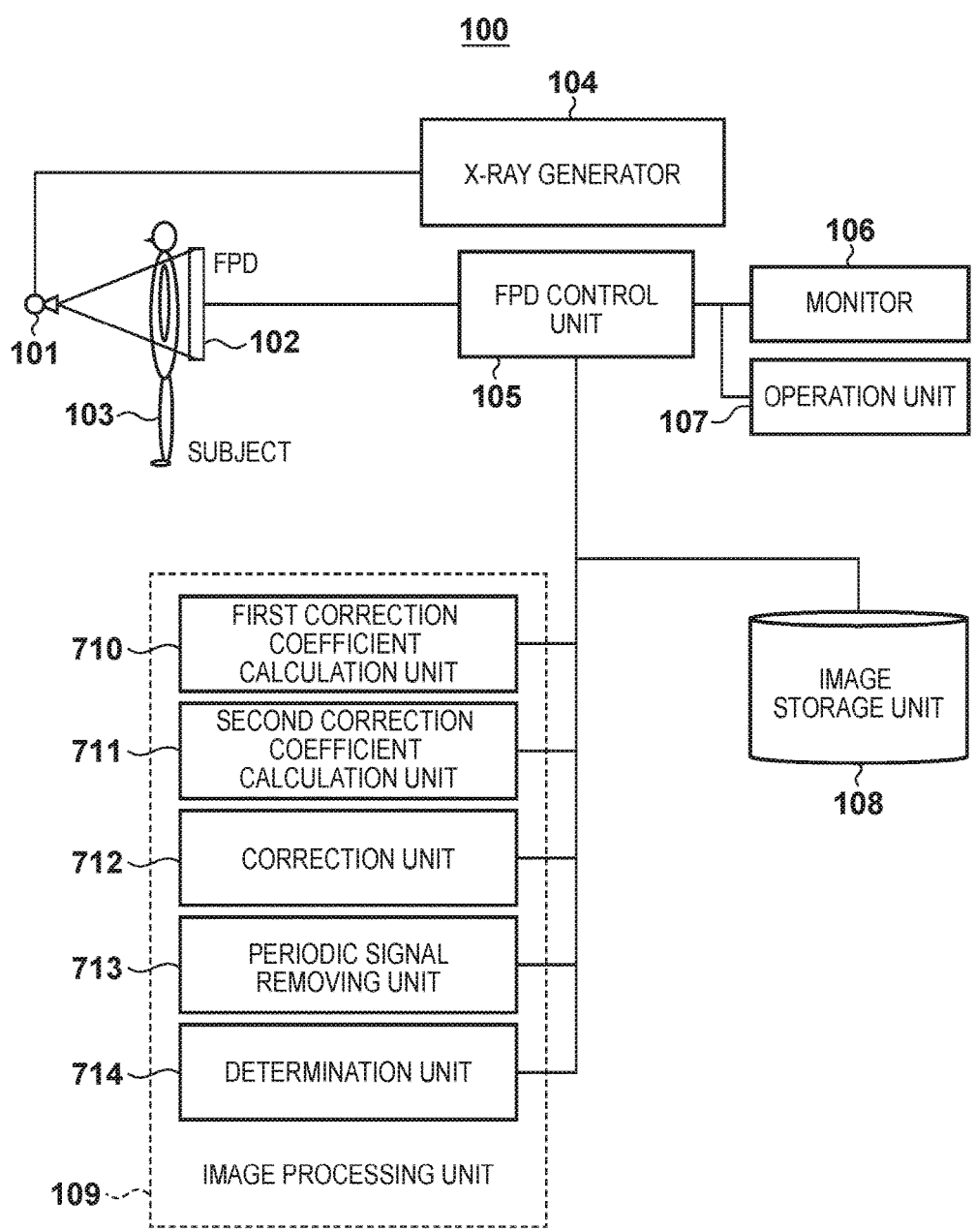
FIG. 7 is a block diagram showing the arrangement of an entire X-ray imaging apparatus according to the second embodiment.

In the second embodiment as well, an example of application to a radiation imaging apparatus that acquires a radiation image from a radiation amount detected by a radiation detection unit configured to detect radiation and performs radiation image processing, for example, an X-ray imaging apparatus 100 as shown in FIG. 7 will be described. The X-ray imaging apparatus 100 has a function of executing X-ray image processing for correcting an X-ray deficiency pixel generated in an X-ray image by an X-ray loss caused by a reset operation when the X-ray image is acquired by automatically detecting X-ray irradiation.

The X-ray imaging apparatus 100 according to the second embodiment is the same as in the first embodiment (FIG. 1) except the arrangement of an image processing unit 109. The image processing unit 109 according to the second embodiment corrects an X-ray deficiency pixel in an image captured by an FPD 102, and includes a first correction coefficient calculation unit 710, a second correction coefficient calculation unit 711, a correction unit 712, a periodic signal removing unit 713, and a determination unit 714.

Figure 8:
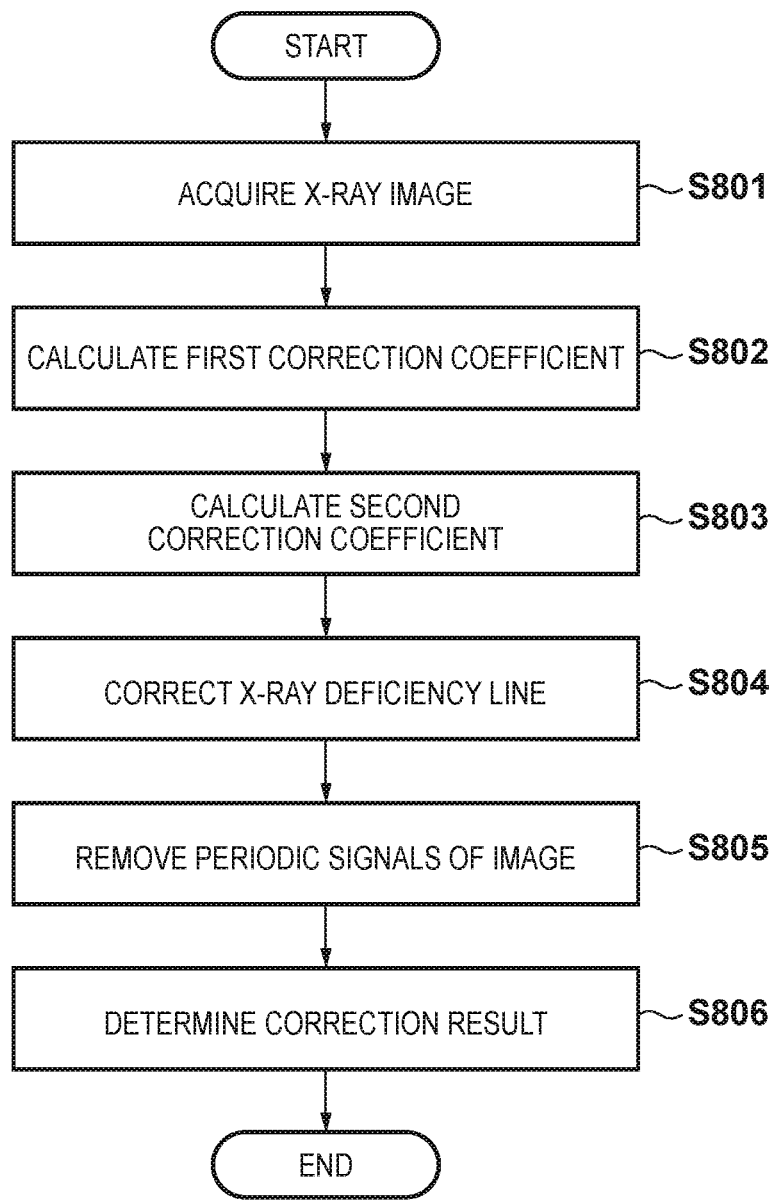
FIG. 8 is a flowchart showing a processing procedure according to the second embodiment.

The operation of a characteristic part of the X-ray imaging apparatus 100 according to the second embodiment with the above-described arrangement will be described in detail with reference to the flowchart shown in FIG. 8. First, an X-ray generator 104 applies a high-voltage pulse to an X-ray tube 101 to irradiate a subject 103 with X-rays. After the start of X-ray irradiation, the FPD 102 automatically detects the X-ray irradiation and thus starts an accumulation operation, thereby acquiring an X-ray image (step S801).

Driving for automatically detecting and determining the start of X-ray irradiation is the same as described above with reference to FIGS. 3 to 5. As described in the first embodiment, a decrease in an output value depends on not only the time lag from the start of X-ray irradiation to the reset operation but also imaging conditions. For example, the larger the X-ray irradiation amount is, the lower the ratio of contribution of charges removed to detect X-ray irradiation to the output value is. Depending on the imaging conditions, the decrease amount may be visually negligible (correction of X-ray deficiency pixels is unnecessary).

As described in the first embodiment, correction coefficients G and D for X-ray deficiency lines are calculated by equation (6). However, since the timing at which X-ray irradiation starts is unknown, the line as the end of X-ray deficiency lines is unknown. In the second embodiment, the lines that have undergone the reset operation are sequentially traced back from the line that has undergone the reset operation at the timing of X-ray irradiation detection, thereby calculating the correction coefficients G and D for ceil (total number of lines/2)−1 lines. For example, in a graph 5b shown in FIG. 5, for the total of 10 lines, the correction coefficients G and D are obtained for four lines, tracing back sequentially from G8 that has undergone the reset operation at the timing of X-ray irradiation detection to G6, G4, and G2, including G2 that is not actually an X-ray deficiency line. Note that the correction target lines may be obtained by tracing back a predetermined number of lines from the line that has undergone the reset operation at the timing of X-ray irradiation detection. In this case, as the predetermined number, a sufficient line count is obtained in advance by calculation or an experiment.

Note that here, the correction coefficients G and D are obtained assuming that the pixels of an X-ray deficiency line and those of an X-ray non-deficiency line that is adjacent and highly correlated with the X-ray deficiency line have almost the same values after correction. However, when the grid is arranged under the condition that the direction of the strips of the grid becomes parallel to the direction of the scanning lines, the correlation with the adjacent X-ray non-deficiency line may be lower, and the assumption does not hold. For this reason, the periodic signals of the grid are superimposed on the correction coefficients. The second correction coefficient calculation unit 711 calculates a correction coefficient by removing the influence of periodic signals caused by the grid from a correction coefficient obtained by the first correction coefficient calculation unit 710 (step S803).

Figure 9A:
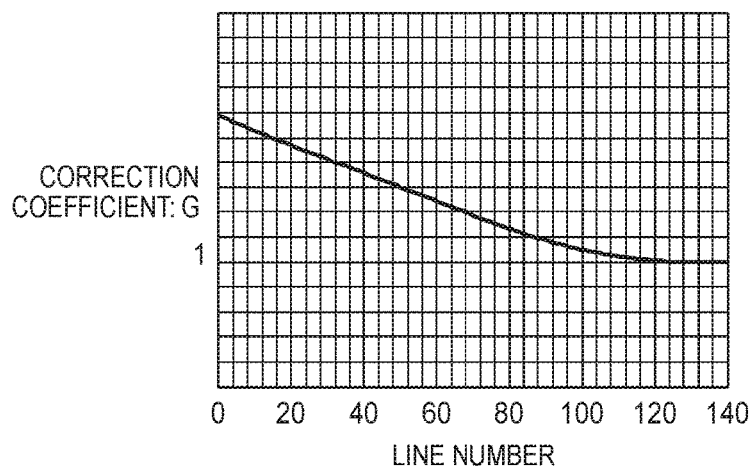
FIG. 9A is a graph for explaining the difference of a correction coefficient caused by the presence/absence of a grid.
Figure 9B:
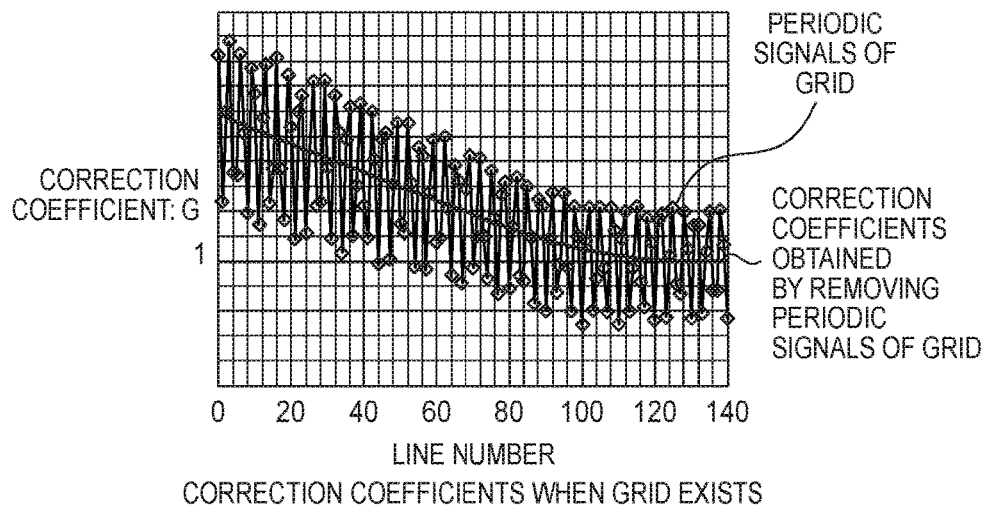
FIG. 9B is a graph for explaining the difference of a correction coefficient caused by the presence/absence of a grid.

When the correction coefficients G calculated by sequentially tracing back the lines that have undergone the reset operation from the line that has undergone the reset operation at the timing of X-ray irradiation detection are plotted, graphs shown in FIGS. 9A and 9B are obtained. Note that in FIGS. 9A and 9B, numbers are sequentially added to the lines starting from line number 0 added to the line that has undergone the reset operation at the timing of X-ray irradiation detection. In a case in which no grid is arranged or a case in which the grid is arranged under the condition that the direction of the stripes of the grid becomes perpendicular to the direction of the scanning lines, the correct correction coefficients G can be calculated, as shown in FIG. 9A. However, if the grid is arranged under the condition that the direction of the strips of the grid becomes parallel to the direction of the scanning lines, the correct correction coefficients G cannot be calculated because periodic signals caused by the grid are superimposed, and the correction coefficient G vibrates, as shown in FIG. 9B. Note that this also applies to the correction coefficients D, although not illustrated. Hence, correction coefficients without such periodic signals are calculated.

In the second embodiment, the periodic signals of the grid are removed using LOWESS. Let i be the line number in FIGS. 9A and 9B, and $G_i$ be the correction coefficient for the line number i. $Gc_i$ without the periodic signals of the grid is calculated for each line using $$Gc_i = a_i \cdot G_i + b_i \quad (19)$$

where $\underline{a}$ and b are unknown. These values are calculated by local regression with respect to the line number i as the center. More specifically, when calculating the regression coefficients $a_i$ and $b_i$ for the line number i, the values are calculated by least square approximation, which minimize an error $E_i$ given by $$E_i = \sum_{k=0}^{N-1} w_k \cdot (G_k - a_i \cdot k - b_i)^2 \quad (20)$$

$$w_k = \begin{cases} \left(1 - \left|\frac{k-i}{d}\right|^3\right)^3, & |k-i| < d \\ 0, & \text{otherwise} \end{cases}$$

Figure 10:
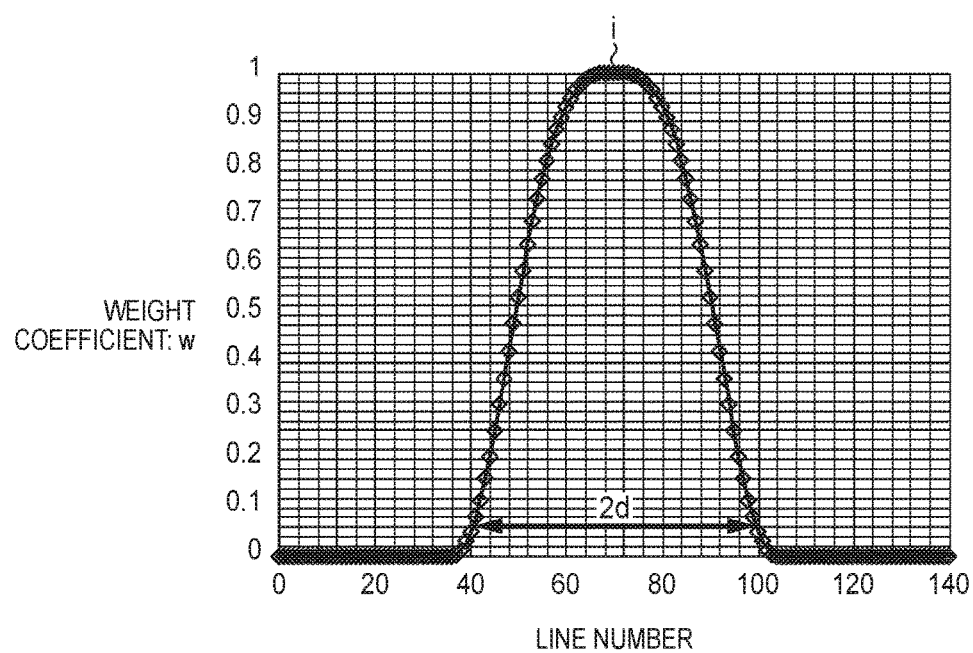
FIG. 10 is a graph for explaining the weight function of local regression.

Note that $w_k$ is a weight function as shown in FIG. 10. The value of this function is 1 for the line number i and becomes small as the distance from a sample k referred from i increases. The value becomes 0 when the distance exceeds d. Hence, the correction coefficient Gc obtained above is a correction coefficient obtained by linearly approximating the correction coefficient G for each line within the range of ±d. Hence, when di is set to a value larger to some extent than the period of the grid, the periodic signals of the grid can be removed, as shown FIG. 9B, because the periodic signals of the grid cannot be applied to a line.

The value d is not particularly limited here. For example, in this embodiment, the value d is set to five times of the period of the grid. Note that the period of the periodic signals of the grid is calculated in advance based on the density of the grid to be placed. The period may be calculated from the power spectrum of the correction coefficient G.

The method of calculating Gc by removing the periodic signals of the grid from the correction coefficient G has been described above. For the correction coefficient D as well, Dc without the periodic signals of the grid is calculated by the same method as described above. In this embodiment, a linear expression is used as the regression equation. However, the present invention is not limited to this, and a polynomial may be used as the regression equation. As the outliers, Robust LOWESS may be used.

In this embodiment, the periodic signals of the grid are removed by smoothing using local regression. Alternatively, smoothing using a low-pass filter or the like. Otherwise, the periodic signals of the grid may be removed by modeling the waveform of correct correction coefficients and fitting the correction coefficients G to the model.

Next, the correction unit 712 corrects the deficiency pixels in the X-ray image using the obtained correction coefficients Gc and Dc (step S804). More specifically, let $\{V_k(i)|i=1, 2, \ldots, n\}$ be the pixel values in the columns i of an X-ray deficiency line k, and $Gc_k$ and $Dc_k$ be the correction coefficients for the line. A pixel value $V'_k(i)$ after correction is calculated for all X-ray deficiency lines by $$V'_k(i) = Gc_k \cdot (V_d(i) - Dc_k) + Dc_k \quad (21)$$

Next, the periodic signal removing unit 713 removes the periodic signals of the grid superimposed on the image by filtering (step S805). More specifically, letting fg (rad/sample) be the frequency of the grid on the image, the grid stripes are removed using an Nth-order FIR filter h calculated by $$h_i = \frac{g\left(i - \frac{N}{2}\right)}{\mu}, \mu = \sum_{i=0}^{N} g\left(i - \frac{N}{2}\right), i \in \quad (22)$$

$$\{0, 1, 2, \ldots, N\}, g(x) = e^{\frac{-x^2}{2\sigma^2}}, \sigma = \frac{3}{f_g}, N = 2 \cdot \lceil 3 \cdot \sigma \rceil$$

Note that the FIR filter calculated by equation (22) is a low-pass filter that blocks frequencies not less than the grid frequency fg. The density of the grid generally used is selected so as to attain a high frequency on the image in consideration of the influence on low-frequency components that form the main structure of the image. The frequency is not less than 0.5π (rad/sample) on the image. In this embodiment, $f_g=0.5\pi$ is set, thereby calculating an FIR filter corresponding to the density of the grid generally used.

Next, the grid is removed using the above-described FIR filter. Note that the purpose here is to remove the grid with stripes parallel to the direction of the scanning lines, filtering is performed using the above-described FIR filter in the direction perpendicular to the scanning lines on the image. Additionally, in this embodiment, since the images before and after the correction are used at the subsequent stage, filtering is performed for both the image before correction and the image corrected by the correction unit 712.

Next, the determination unit 714 determines whether the correction performed in step S804 is appropriate (step S806). More specifically, assuming that the pixels of an X-ray deficiency line and those of an X-ray non-deficiency line close to the X-ray deficiency line have almost the same values after correction, it is determined whether the corrected image is appropriate.

Figure 11A:
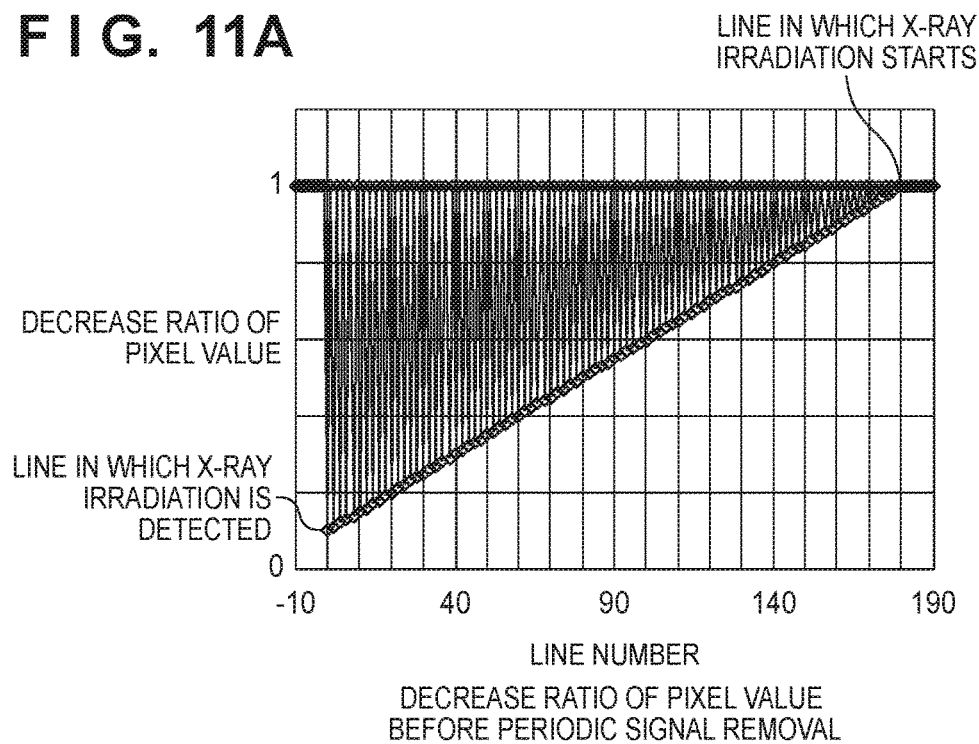
FIG. 11A is a graph for explaining the decrease ratio of a pixel value.
Figure 11B:
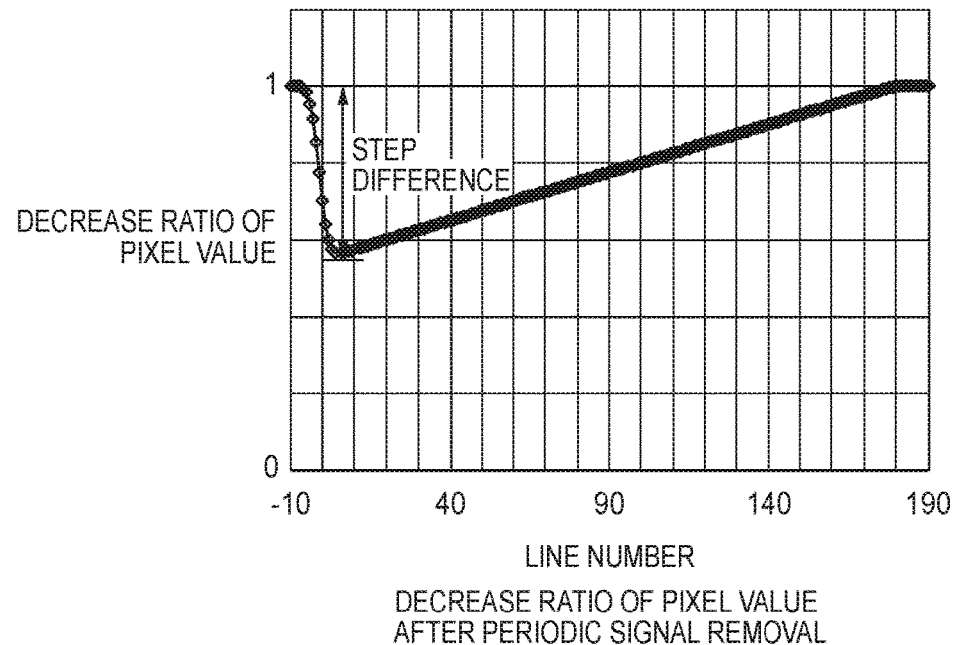
FIG. 11B is a graph for explaining the decrease ratio of a pixel value.

In the driving according to this embodiment, as described above, the decrease ratio of the pixel value is lowest in the line at which X-ray irradiation is detected. The decrease ratio gradually becomes low and is minimized in the line at which X-ray irradiation has started. In addition, X-ray deficiency lines are generated for every other line. When the decrease ratios of pixel values are plotted, a graph shown in FIG. 11A is obtained (in FIGS. 11A and 11B, the line number of the line at which X-ray irradiation has been detected is set to 0). When the above-described periodic signal removal is performed, the vibration components on every other line, which have the peak at the Nyquist frequency are removed together with the periodic signals of the grid, and a wedge-shaped waveform as shown in FIG. 11B is obtained.

In this embodiment, whether the correction has appropriately been performed is evaluated by evaluating the step difference of the wedge-shaped waveform. More specifically, let $\{x_i|i=1, 2, \ldots, n\}$ be the pixel values in columns i of the line at which X-ray irradiation is detected, and $\{y_{i,m}|i=1, 2, \ldots, n\}$ be the pixel values in the columns i of an X-ray non-deficiency line apart downward (leftward in FIG. 11B) by m lines on the image. When the pixel values of each column of the lines are assumed to be almost the same if the correction has appropriately been performed, the relationship between a pixel value x of the X-ray deficiency line and a pixel value y of the X-ray non-deficiency line is given by $$y_{i,m} = x_i \quad (23)$$

Hence, a gradient $\underline{a}$ that minimizes an error E given by equation (24) is obtained by least square approximation. If the gradient $\underline{a}$ is almost 1, it can be determined that appropriate correction is performed.

$$E = \sum_{i=1}^{n} (y_{i,m} - a \cdot x_i)^2 \quad (24)$$

Here, m can be set to an arbitrary value, which is not particularly limited but is set to, for example, 10 in this embodiment.

Note that in this embodiment, whether correction may lead to poorer image quality is determined. When the gradient $\underline{a}$ is obtained by equation (24) for a line at which X-ray irradiation has been detected before and after correction. If the gradient after the correction approaches 1 with respect to the gradient before the correction, that is, if the step difference becomes small, it is determined that the correction is appropriate. More specifically, let $a_o$ be the gradient obtained from the line before the correction in step S804, and $a_c$ be the gradient obtained from the line after the correction in step S804, the correction is determined to be appropriate when the following conditions are met.

$$|a_c-1|<|a_o-1| \quad (25)$$

The correction is not appropriately performed when the influence of periodic signals caused by the grid is large. That is, if correction coefficients as shown in FIG. 9A are obtained by the first correction coefficient calculation unit 710, correction is appropriately performed. Even when the periodic signals caused by the periodic signal are superimposed, as shown in FIG. 9B, if the amplitude or period of the grid is small relative to the wedge-shaped waveform to be obtained, the influence is small, and correction can appropriately be performed. Hence, only when the influence of the periodic signals caused by the grid is large, determination by inequality (25) is performed, thereby raising the determination accuracy.

Hence, in this embodiment, using the correction coefficient G calculated by the first correction coefficient calculation unit 710 and the correction coefficient Gc calculated by the second correction coefficient calculation unit 711, it is determined whether the influence of the periodic signals caused by the grid is large. More specifically, letting $G_i$ and $Gc_i$ be the correction coefficients for the line number i, a coefficient $R^2$ of determination is calculated by $$R^2 = 1 - \frac{\sum_{i=0}^{N}(G_i - Gc_i)^2}{\sum_{i=0}^{N}(G_i - \overline{G})^2}, \overline{G} = \frac{1}{N+1}\sum_{i=0}^{N} G_i \qquad (26)$$

The coefficient $R^2$ of determination takes a value of 0 to 1. The larger the difference between the correction coefficients G and Gc is, the smaller the coefficient $R^2$ of determination is. Hence, when the periodic signals caused by the grid are superimposed, as shown in FIG. 9B, and the influence of the periodic signals is large, the coefficient $R^2$ of determination consequently takes a small value. Hence, the influence of the grid is determined to be large under a condition represented by $$R^2 < TH \qquad (27)$$

where TH is a threshold used to determine the degree of the influence of the grid, which is set to, for example, 0.95 in this embodiment.

It is determined using the above-described two determination criteria whether the correction is appropriate. More specifically, if inequality (27) is met, and inequality (25) is not met, it is determined that the correction has not appropriately been performed. Otherwise, it is determined that the correction has appropriately been performed. Note that whether the correction is appropriate may be determined using only one of inequalities (25) and (27).

In this embodiment, upon determining that the correction has not appropriately been performed, the correction result is rejected, and the image before correction is stored in an image storage unit 108 as processed data. This makes it possible to reduce the possibility that the correction results in poorer image quality. Note that a case in which correction cannot appropriately be performed is a case in which the amplitude or period of the grid is large relative to the wedge-shaped waveform to be obtained, as described above. In other words, in many cases, the wedge-shaped waveform as the correction target is relatively very small, and the decrease amount is visually negligible even without correction.

Note that upon determining that the correction has not appropriately been performed, the image before correction is stored in the image storage unit 108 as processed data, and additionally, the operator may be explicitly notified via a monitor 106 that the correction could not be executed.

Third Embodiment

Figure 12:
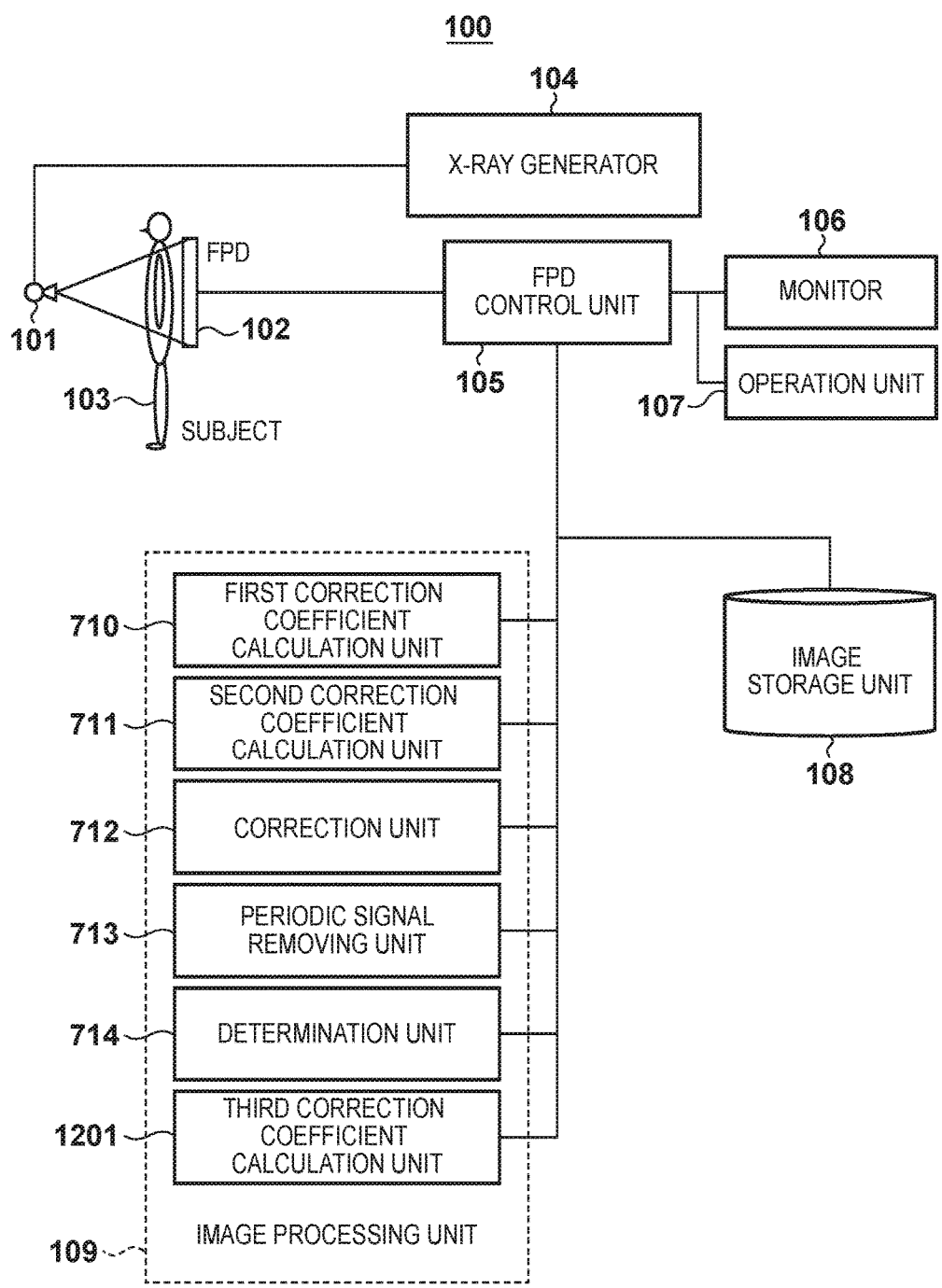
FIG. 12 is a block diagram showing the arrangement of an entire X-ray imaging apparatus according to the third embodiment.
Figure 13:
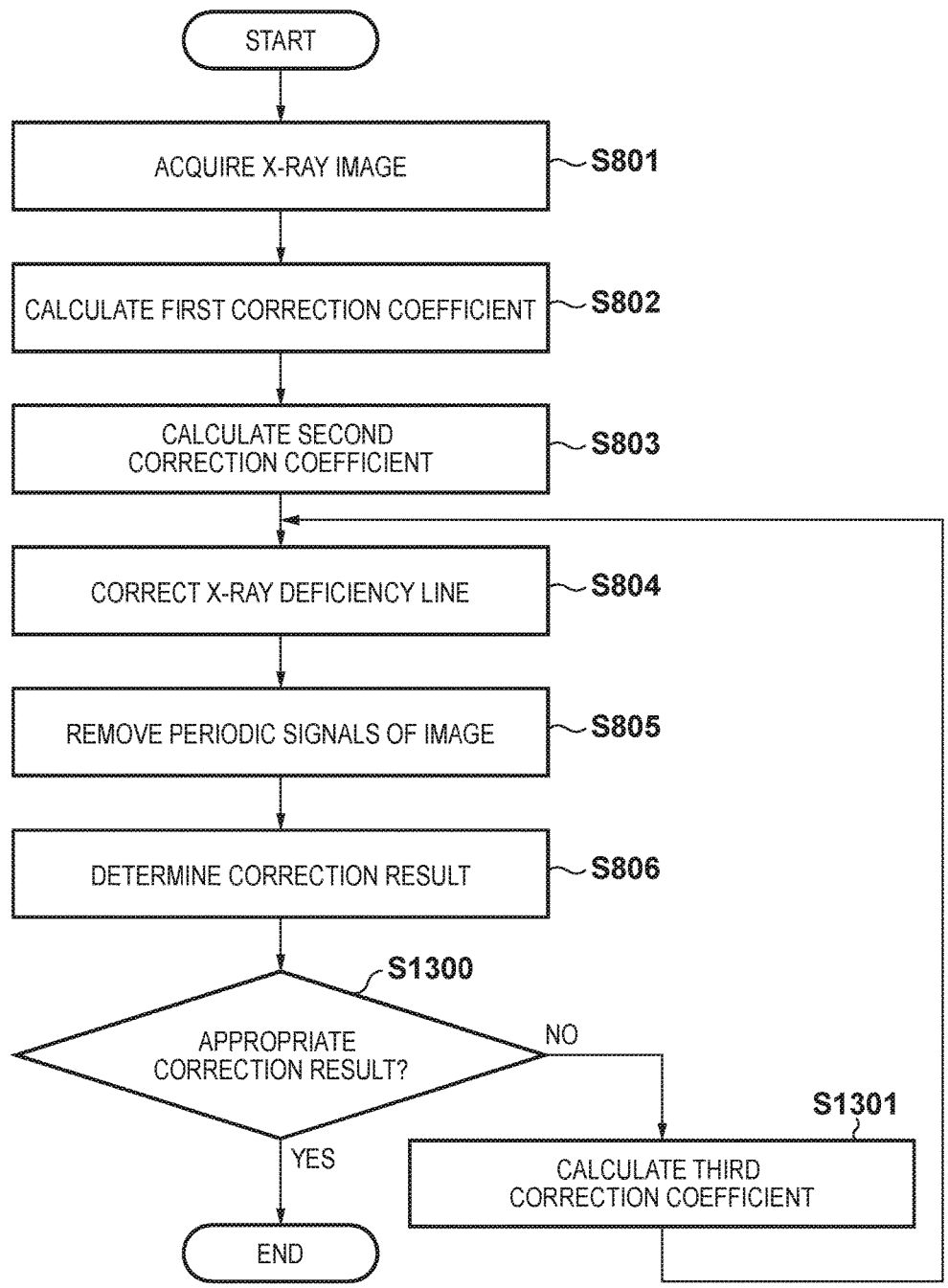
FIG. 13 is a flowchart showing a processing procedure according to the third embodiment.

The present invention is applied to, for example, an X-ray imaging apparatus 100 as shown in FIG. 12. As compared to the X-ray imaging apparatus 100 shown in FIG. 7, the X-ray imaging apparatus 100 shown in FIG. 12 includes a third correction coefficient calculation unit 1201. In the third embodiment, as the processing procedure of an image processing unit 109, an operation is performed in accordance with the flowchart shown in FIG. 13 different from the second embodiment.

Note that the same reference numerals as in the X-ray imaging apparatus 100 shown in FIG. 7 denote parts that similarly operate in the X-ray imaging apparatus 100 shown in FIG. 12, and a detailed description thereof will be omitted. In addition, the same step numbers as in the flowchart shown in FIG. 8 denote steps that similarly execute processes in the flowchart shown in FIG. 13, and an arrangement different from the above-described second embodiment will be described here in detail. In steps S801 to S806, the same processes as in the second embodiment are executed, and it is determined whether correction in step S804 is appropriate.

In the second embodiment, upon determining that the correction has not appropriately been performed, the image before correction is stored in the image storage unit 108 as processed data. In this embodiment, however, upon determining that the correction has not appropriately been performed (NO ins step S1300), the third correction coefficient calculation unit 1201 calculates the correction coefficient again (step S1301).

As described above, correction is not appropriately performed probably because the influence of periodic signals caused by a grid is large, and as the result, the second correction coefficient calculation unit 711 cannot sufficiently remove the influence. The third correction coefficient calculation unit 1201 calculates the correction coefficient by LOWESS, like the second correction coefficient calculation unit 711. By changing a parameter used at this time, the third correction coefficient calculation unit 1201 calculates the correction coefficient by more strongly removing the influence of the periodic signals caused by the grid.

More specifically, d in equation (20) described above is made large, and the correction coefficient is calculated again. Here, d is a parameter to set a width to perform linear regression. When this value is made larger, the influence of periodic signals can more strongly be removed. Note that if the value is made too large, fitting to a correct correction coefficient deteriorates. Hence, they have tradeoff relationships.

In this embodiment, d is sequentially increased, and an optimum solution for appropriate correction is obtained. More specifically, the width is increased by, for example, 5% with respect to d set by the second correction coefficient calculation unit 711, and the correction coefficient is calculated (step S1301). Next, in step S804, X-ray deficiency lines are corrected using the newly obtained correction coefficient. Then, in steps S805 and S806, the correction result is determined. If the correction result is not appropriate (step S1300), the width of d is further increased by 5%, and a correction result is obtained again (step S1301).

The above-described operation is repetitively executed until the correction result is determined to be appropriate. It is therefore possible to perform appropriate correction even if the influence of periodic signals caused by the grid is large.

As described above, according to the second and third embodiments, it is determined whether a radiation deficiency pixel generated when a radiation image is acquired by automatically detecting radiation irradiation is appropriately corrected, thereby suppressing degradation in image quality caused by inappropriate correction.

Note that in the second and third embodiments, a case in which correction target lines in which correction target pixels are arranged and non-correction target lines in which non-correction target pixels are arranged alternately exist has been described. However, the present invention is not limited to this. For example, the correction and noise level reduction according to the embodiments can be applied to any image in which correction target pixels with an X-ray loss are arranged so as to be correctable by non-correction target pixels without an X-ray loss. Hence, for example, the processing may be applied to not an arrangement that performs reset on a line basis but an arrangement that performs reset on a column basis. The above-described processing is also applicable to an X-ray image in which, for example, correction target pixels and non-correction target pixels are arrayed in a checkered pattern, as a matter of course. In the above embodiments, an example in which reset is performed for each line as the reset operation on a line basis has been described. However, a plurality of even-numbered lines or odd-numbered lines (for example, "G2 and G4" and "G6 and G8) in FIG. 5) may simultaneously be reset.

In the second and third embodiments, a case in which periodic signals formed by insertion of a grid are removed has been described. However, the present invention is not limited to this Preferred embodiments of the present invention have been described above. However, the present invention is not limited to these embodiments, as a matter of course, and various changes and modifications can be made within the scope of the present invention.

The present invention also incorporates a case in which the functions of the above-described embodiments are achieved by supplying a software program (a program corresponding to the illustrated flowchart in each embodiment) to a system or apparatus directly or from a remote site and causing the computer of the system or apparatus to read out and execute the supplied program code.

Hence, the program code itself, which is installed in the computer to implement the functions and processing of the present invention by the computer, also implements the present invention. That is, the present invention incorporates the computer program itself for implementing the functions and processing of the present invention.

Examples of the computer-readable recording medium to supply the program are a hard disk, optical disk, magnetooptical disk, MO, CD-ROM, CD-R, CD-RW, magnetic tape, nonvolatile memory card, ROM, and DVD (DVD-ROM or DVD-R).

As another program supply method, a client computer may be connected to a homepage on the Internet by using a browser to download the computer program of the present invention itself or a compressed file including an automatic installation function from the homepage to a recording medium such as a hard disk. The program code that constitutes the program of the present invention may be divided into a plurality of files, and the files may be downloaded from different homepages. That is, the present invention also incorporates a WWW server which causes a plurality of users to download a program file that implements the functions and processing of the present invention by a computer.

The program of the present invention may be encrypted, stored in a storage medium such as a CD-ROM, and delivered to users. Any user who satisfies predetermined conditions may be allowed to download key information for decryption from a homepage via the Internet so that he/she can execute the encrypted program by using the key information and install the program in the computer.

The functions of the above-described embodiments can be implemented not only when the computer executes the readout program but also when, e.g., the OS running on the computer partially or wholly executes actual processing.

The present invention is not limited to the above embodiments, and various changes and modifications can be made within the spirit and scope of the present invention. Therefore, to apprise the public of the scope of the present invention, the following claims are made.

What is claimed is:

1. A radiation imaging apparatus comprising:
an acquisition unit configured to acquire a radiation image from radiation detected by a radiation detection unit;
a correction coefficient calculation unit configured to calculate a correction coefficient to correct a pixel value of a first pixel that is a correction target in the radiation image by referring to a pixel value of a second pixel other than the first pixel;
a correction unit configured to correct the pixel value of the first pixel by amplifying the pixel value of the first pixel using the correction coefficient;
a calculation unit configured to calculate an evaluation value that evaluates an amplification in a noise level caused when the first pixel is corrected by amplifying the pixel value of the first pixel; and
a reduction unit configured to perform processing of reducing the noise level for the first pixel after the correction based on the evaluation value calculated by the calculation unit.

2. The radiation imaging apparatus according to claim 1, wherein the correction coefficient calculation unit acquires the correction coefficient by performing regression analysis of a relationship between a pixel value of the first pixel and a pixel value of the second pixel adjacent to the first pixel.

3. A radiation image processing apparatus comprising:
a correction coefficient calculation unit configured to calculate a correction coefficient to correct a pixel value of a first pixel that is a correction target in a radiation image by referring to a pixel value of a second pixel other than the first pixel;
a correction unit configured to correct the pixel value of the first pixel by amplifying the pixel value of the first pixel using the correction coefficient;
a calculation unit configured to calculate an evaluation value that evaluates an amplification in a noise level caused when the first pixel is corrected by amplifying the pixel value of the first pixel; and
a reduction unit configured to perform processing of reducing the noise level for the first pixel after the correction based on the evaluation value calculated by the calculation unit.

4. A method of controlling a radiation imaging apparatus, the method comprising:
acquiring a radiation image from radiation detected by a radiation detection unit;
calculating a correction coefficient to correct a pixel value of first pixel that is a correction target in the radiation image by referring to a pixel value of a second pixel other than the first pixel;
correcting the pixel value of the first pixel by amplifying the pixel value of the first pixel using the correction coefficient;
calculating an evaluation value that evaluates an amplification in a noise level caused when the first pixel is corrected by amplifying the pixel value of the first pixel; and
performing processing of reducing the noise level for the first pixel after the correction based on the calculated evaluation value.

5. A radiation image processing method comprising:
calculating a correction coefficient to correct a pixel value of first pixel that is a correction target in a radiation image by referring to a pixel value of a second pixel other than the first pixel;
correcting the pixel value of the first pixel by amplifying the pixel value of the first pixel using the correction coefficient;
calculating an evaluation value that evaluates an amplification in a noise level caused when the first pixel is corrected by amplifying the pixel value of the first pixel; and
performing processing of reducing the noise level for the first pixel after the correction based on the calculated evaluation value.

6. A non-transitory computer-readable storage medium storing a computer program for causing a computer to execute a method of controlling a radiation imaging apparatus, the method comprising:
acquiring a radiation image from radiation detected by a radiation detection unit;
calculating a correction coefficient to correct a pixel value of first pixel that is a correction target in the radiation image by referring to a pixel value of a second pixel other than the first pixel;
correcting the pixel value of the first pixel by amplifying the pixel value of the first pixel using the correction coefficient;
calculating an evaluation value that evaluates an amplification in a noise level caused when the first pixel is corrected by amplifying the pixel value of the first pixel; and
performing processing of reducing the noise level for the first pixel after the correction based on the calculated evaluation value.

7. A non-transitory computer-readable storage medium storing a computer program for causing a computer to execute a radiation image processing method comprising:
calculating a correction coefficient to correct a pixel value of first pixel that is a correction target in a radiation image by referring to a pixel value of a second pixel other than the first pixel;
correcting the pixel value of the first pixel by amplifying the pixel value of the first pixel using the correction coefficient;
calculating an evaluation value that evaluates an amplification in a noise level caused when the first pixel is corrected by amplifying the pixel value of the first pixel; and
performing processing of reducing the noise level for the first pixel after the correction based on the calculated evaluation value.

8. A radiation imaging apparatus comprising:
an acquisition unit configured to acquire a radiation image from radiation detected by a radiation detection unit;
a correction unit configured to correct a first pixel that is a correction target in the radiation image by referring to a second pixel other than the first pixel;
a calculation unit configured to calculate an evaluation value that evaluates an increase in a noise level caused when the first pixel is corrected by the correction unit; and
a reduction unit configured to perform processing of reducing the noise level for the first pixel after the correction based on the evaluation value calculated by the calculation unit, wherein the correction unit acquires a correction coefficient by performing regression analysis of a relationship between a pixel value of the first pixel and a pixel value of the second pixel adjacent to the first pixel and corrects the first pixel using the correction coefficient.

9. The radiation imaging apparatus according to claim 8, wherein the calculation unit calculates the evaluation value based on a noise level increased, upon the correction by the correction unit, from the noise level in a radiation amount corresponding to the pixel value of the first pixel before the correction and a noise level in a radiation amount corresponding to the pixel value of the first pixel after the correction.

10. The radiation imaging apparatus according to claim 9, wherein the noise level is a standard deviation of noise.

11. The radiation imaging apparatus according to claim 10, wherein letting $\sigma Q$ be a standard deviation of quantum noise dependent on the radiation amount, $\sigma S$ be a standard deviation of system noise independent of the radiation amount, G be a magnification of the correction by the correction unit, and X be the radiation amount corresponding to the pixel value after the correction, the calculation unit obtains the evaluation value by $$W = \sqrt{\frac{G \cdot \sigma_Q^2 \cdot X + G^2 \cdot \sigma_S^2}{\sigma_Q^2 \cdot X + \sigma_S^2}}$$

12. The radiation imaging apparatus according to claim 8, wherein the reduction unit reduces the noise level such that the noise level of the first pixel after the correction becomes equivalent to the noise level of the second pixel adjacent to the first pixel.

13. The radiation imaging apparatus according to claim 8, wherein the reduction unit reduces the noise level by applying a filter decided based on the evaluation value to the first pixel after the correction.

14. The radiation imaging apparatus according to claim 13, wherein the reduction unit reduces the noise level of the first pixel after the correction by filtering for a plurality of adjacent second pixels.

15. The radiation imaging apparatus according to claim 8, wherein the first pixel is a pixel in which information of the radiation is lost by a reset operation of the radiation detection unit.

16. The radiation imaging apparatus according to claim 8, wherein the radiation image has a portion where correction target lines, in which the first pixels are arranged, and non-correction target lines, in which the second pixels are arranged, alternately exist.

17. The radiation imaging apparatus according to claim 16, further comprising a determination unit configured to determine a start of irradiation of the radiation based on a signal read out at the time of reset while resetting the radiation detection unit on a line basis, wherein
the reset is repeated during a time after the radiation detection unit is irradiated with the radiation until the determination unit determines the start of irradiation, thereby generating the portion where the correction target lines and the non-correction target lines in the radiation image alternately exist in the radiation image.

18. The radiation imaging apparatus according to claim 17, wherein the correction unit decides, for each correction target line, the correction coefficient of the correction target line by performing linear regression analysis of a relationship with an adjacent non-correction target line, and corrects a pixel of the correction target line using the correction coefficient.

19. The radiation imaging apparatus according to claim 18, wherein the correction target line is selected by tracing back an order of execution of the reset from a line determined as the start of irradiation by the determination unit, and
lines up to a line at which a correction amount of the pixel value represented by the correction coefficient falls within a predetermined range are selected as the correction target lines.

20. A radiation imaging apparatus comprising:
a determination unit configured to determine a start of irradiation of the radiation while resetting a line of pixels in a radiation detection unit every other line;
an acquisition unit configured to acquire a radiation image from radiation detected by the radiation detection unit;
a correction unit configured to correct first pixels that are a correction target line in the radiation image by referring to second pixels that are a non-correction target line;
a calculation unit configured to calculate an evaluation value that evaluates an increase in a noise level caused when the first pixels is corrected by the correction unit; and
a reduction unit configured to perform processing of reducing the noise level for the first pixels after the correction based on the evaluation value calculated by the calculation unit, wherein
the reset is repeated during a time after the radiation detection unit is irradiated with the radiation until the determination unit determines the start of irradiation, thereby correction target lines and non-correction target lines in the radiation image alternately exist in the radiation image.

21. A method of controlling a radiation imaging apparatus, the method comprising:
acquiring a radiation image from radiation detected by a radiation detection unit;
correcting a first pixel that is a correction target in the radiation image by referring to a second pixel other than the first pixel;
calculating an evaluation value that evaluates an increase in a noise level caused when the first pixel is corrected; and
performing processing of reducing the noise level for the first pixel after the correction based on the calculated evaluation value, wherein
in the correcting the first pixel, a correction coefficient is acquired by performing regression analysis of a relationship between a pixel value of the first pixel and a pixel value of the second pixel adjacent to the first pixel and the first pixel is corrected using the correction coefficient.

22. A method of controlling a radiation imaging apparatus, the method comprising:
determining a start of irradiation of the radiation while resetting a line of pixels in a radiation detection unit every other line;
acquiring a radiation image from radiation detected by the radiation detection unit;
correcting first pixels that are a correction target line in the radiation image by referring to second pixels that are a non-correction target line;
calculating an evaluation value that evaluates an increase in a noise level caused when the first pixels is corrected; and
performing processing of reducing the noise level for the first pixels after the correction based on the calculated evaluation value, wherein
the reset is repeated during a time after the radiation detection unit is irradiated with the radiation until the determination unit determines the start of irradiation, thereby correction target lines and non-correction target lines in the radiation image alternately exist in the radiation image.

23. A non-transitory computer-readable storage medium storing a computer program for causing a computer to execute a method of controlling a radiation imaging apparatus, the method comprising:
acquiring a radiation image from radiation detected by a radiation detection unit;
correcting a first pixel that is a correction target in the radiation image by referring to a second pixel other than the first pixel;
calculating an evaluation value that evaluates an increase in a noise level caused when the first pixel is corrected; and
performing processing of reducing the noise level for the first pixel after the correction based on the calculated evaluation value, wherein
in the correcting the first pixel, a correction coefficient is acquired by performing regression analysis of a relationship between a pixel value of the first pixel and a pixel value of the second pixel adjacent to the first pixel and the first pixel is corrected using the correction coefficient.

24. A non-transitory computer-readable storage medium storing a computer program for causing a computer to execute a method of controlling a radiation imaging apparatus, the method comprising:
determining a start of irradiation of the radiation while resetting a line of pixels in a radiation detection unit every other line;
acquiring a radiation image from radiation detected by the radiation detection unit;
correcting first pixels that are a correction target line in the radiation image by referring to second pixels that are a non-correction target line;
calculating an evaluation value that evaluates an increase in a noise level caused when the first pixels is corrected; and
performing processing of reducing the noise level for the first pixels after the correction based on the calculated evaluation value, wherein
the reset is repeated during a time after the radiation detection unit is irradiated with the radiation until the determination unit determines the start of irradiation, thereby correction target lines and non-correction target lines in the radiation image alternately exist in the radiation image.

* * * * *